US012584964B2

(12) United States Patent
Kim et al.

(10) Patent No.: US 12,584,964 B2
(45) Date of Patent: Mar. 24, 2026

(54) SYSTEM FOR DIAGNOSING DRY ELECTRODE MIXTURE

(71) Applicants:HYUNDAI MOTOR COMPANY, Seoul (KR); KIA CORPORATION, Seoul (KR)

(72) Inventors: Hyun Jin Kim, Daegu (KR); Han Nah Song, Ansan-si (KR)

(73) Assignees: HYUNDAI MOTOR COMPANY, Seoul (KR); KIA CORPORATION, Seoul (KR)

( * ) Notice: Subject to any disclaimer, the term of this patent is extended or adjusted under 35 U.S.C. 154(b) by 420 days.

(21) Appl. No.: 18/207,890

(22) Filed: Jun. 9, 2023

(65) Prior Publication Data

US 2024/0183906 A1     Jun. 6, 2024

(30) Foreign Application Priority Data

Dec. 5, 2022    (KR) ......................... 10-2022-0167269

(51) Int. Cl.
| | |
|---|---|
| *G01R 31/367* | (2019.01) |
| *G01N 11/02* | (2006.01) |
| *G01R 31/389* | (2019.01) |
| *H01M 4/04* | (2006.01) |
| *H01M 4/62* | (2006.01) |
| *G01N 33/00* | (2006.01) |
| *H01M 10/0525* | (2010.01) |

(52) U.S. Cl.
CPC ........... *G01R 31/367* (2019.01); *G01N 11/02* (2013.01); *G01R 31/389* (2019.01); *H01M*

*4/0435* (2013.01); *H01M 4/623* (2013.01); *G01N 33/0091* (2024.05); *H01M 10/0525* (2013.01)

(58) Field of Classification Search
CPC ................ G01R 31/367; G01R 31/389; G01R 31/3865; G01N 11/02; G01N 33/0091; G01N 27/04; G01N 2011/0033; H01M 4/0435; H01M 4/623; H01M 10/0525; H01M 4/13; H01M 10/052; H01M 4/04; H01M 4/139; G06N 3/04; G06N 3/08
See application file for complete search history.

(56) References Cited

U.S. PATENT DOCUMENTS

| | | | | |
|---|---|---|---|---|
| 11,906,424 B2* | 2/2024 | Jarrahi | ...................... | G01J 3/42 |
| 2004/0130338 A1* | 7/2004 | Wang | ..................... | G01N 27/24 |
| | | | | 324/694 |
| 2012/0232810 A1* | 9/2012 | Kaipio | ................... | G01N 27/06 |
| | | | | 702/45 |

FOREIGN PATENT DOCUMENTS

| | | | | |
|---|---|---|---|---|
| GB | 2546522 | * | 7/2017 | ............... G01F 1/64 |
| KR | 2020-0138263 A | | 12/2020 | |
| KR | 10-2238248 B1 | | 4/2021 | |

* cited by examiner

*Primary Examiner* — Tung S Lau
(74) *Attorney, Agent, or Firm* — MCDONNELL BOEHNEN HULBERT & BERGHOFF LLP

(57) ABSTRACT

A method of diagnosing a dry electrode mixture includes manufacturing the dry electrode mixture, inputting a feature value of the manufactured dry electrode mixture to a deep learning model, and acquiring a manufacturing condition of the dry electrode mixture from the deep learning model by input of the feature value.

16 Claims, 9 Drawing Sheets

1

30

60

50

70

20

| FLOW PROPERTY MEASUREMENT APPARATUS | | CONTROLLER | | MANUFACTURING APPARATUS |

CONTROLLER

MEMORY    PROCESSOR

FLOW PROPERTY
MEASUREMENT APPARATUS

ELECTRICAL CONDUCTIVITY
MEASUREMENT APPARATUS

MANUFACTURING
APPARATUS

DEEP LEARNING MODEL

| COLLECT DATA ON DRY ELECTRODE MIXTURES | S60 |

↓

| TRAIN SYSTEM | S62 |

↓

| GENERATE DEEP LEARNING MODEL OF SYSTEM | S64 |

FIG. 8

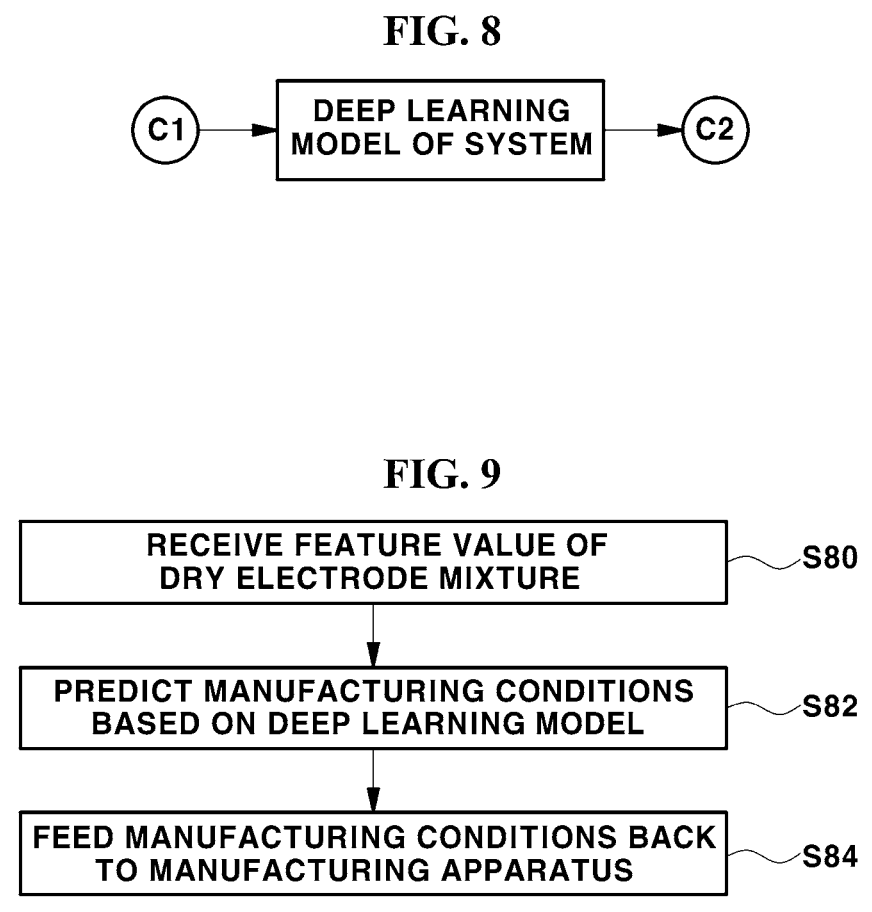

C1 → DEEP LEARNING MODEL OF SYSTEM → C2

FIG. 9

RECEIVE FEATURE VALUE OF
DRY ELECTRODE MIXTURE      S80

PREDICT MANUFACTURING CONDITIONS
BASED ON DEEP LEARNING MODEL      S82

FEED MANUFACTURING CONDITIONS BACK
TO MANUFACTURING APPARATUS      S84

SYSTEM FOR DIAGNOSING DRY ELECTRODE MIXTURE

CROSS REFERENCE TO RELATED APPLICATIONS

This application claims under 35 U.S.C. § 119(a) the benefit of priority to Korean Patent Application No. 10-2022-0167269 filed on Dec. 5, 2022, the entire contents of which are incorporated herein by reference.

BACKGROUND

(a) Technical Field

The present disclosure relates to a secondary battery, and more particularly, to a dry electrode for secondary batteries.

(b) Background Art

Recently, application of rechargeable secondary batteries is being gradually expanded to various fields. Particularly, in order to keep pace with rapid growth of electric vehicles, research and development of secondary batteries are being actively carried out.

Electrodes of the secondary batteries are generally manufactured through a wet process. In the wet process, a slurry is manufactured by dissolving electrode materials, a binder and a conductive material, which are included in an electrode, in a solvent. However, a dry process, which may increase the energy density of a battery compared to the wet process without using such a solvent required in the wet process, has recently been introduced.

In the dry process of manufacturing an electrode, an electrode material mixture is prepared by mixing electrode materials without any solvent. A dry electrode film is formed by pressing or calendaring. Manufacture of the electrode is completed by bonding the formed dry electrode film to a current collector.

Since manufacture of an electrode using the dry process is in an introductory phase of technology life cycle or at an early stage, technology to evaluate the quality of the manufactured electrode is hard to find. Therefore, a defect may be found at the final stage of the manufacturing process of the electrode. Under these circumstances, the process needs to be returned to the first stage to solve the cause of occurrence of the defect. Further, in order to determine the cause of occurrence of the defect, a lot of time and expense are required.

The above information disclosed in this Background section is only for enhancement of understanding of the background of the disclosure and therefore it may contain information that does not form the prior art that is already known to a person of ordinary skill in the art.

SUMMARY

The present disclosure has been made in an effort to solve the above-described problems associated with the prior art, and it is an object of the present disclosure to provide a system for diagnosing a dry electrode mixture, which may evaluate inherent conditions of the dry electrode mixture only using physical feature values through deep learning.

In one aspect, the present disclosure provides a method of diagnosing a dry electrode mixture, including manufacturing the dry electrode mixture, inputting a feature value of the manufactured dry electrode mixture to a deep learning model, and acquiring a manufacturing condition of the dry electrode mixture from the deep learning model by input of the feature value.

In another aspect, the present disclosure provides a system for diagnosing a dry electrode mixture, including a memory including commands, and a processor configured to execute the commands, wherein the processor executes the commands to receive a feature value of the dry electrode mixture manufactured, to input the feature value to a deep learning model, and to output a manufacturing condition of the dry electrode mixture from the deep learning model by input of the feature value.

In still another aspect, the present disclosure provides a system for diagnosing a dry electrode mixture, including a manufacturing apparatus configured to manufacture the dry electrode mixture, a flow property measurement apparatus configured to evaluate flow property of the dry electrode mixture, an electrical conductivity measurement apparatus configured to measure electrical conductivity of the dry electrode mixture, and a controller configured to receive at least one of the flow property or the electrical conductivity of the dry electrode mixture and to output a manufacturing condition of the dry electrode mixture based on a deep learning model.

Other aspects and preferred embodiments of the disclosure are discussed infra.

BRIEF DESCRIPTION OF THE FIGURES

The above and other features of the present disclosure will now be described in detail with reference to certain exemplary embodiments thereof illustrated in the accompanying drawings which are given hereinbelow by way of illustration only, and thus are not limitative of the present disclosure, and wherein:

FIG. 3 is a graph representing results of flow property evaluation of certain dry electrode mixtures;

FIGS. 4A, 4B, and 4C are a graph representing results of flow property evaluation of certain dry electrode mixtures, and images of the arbitrary mixtures acquired by scanning electron microscopy (SEM);

FIG. 8 is a schematic view showing input variables and output variables of the deep learning model of the system according to some embodiments of the present disclosure; and FIG. 9 is a flowchart representing operation of the system according to some embodiments of the present disclosure.

Figures 1, 2A:
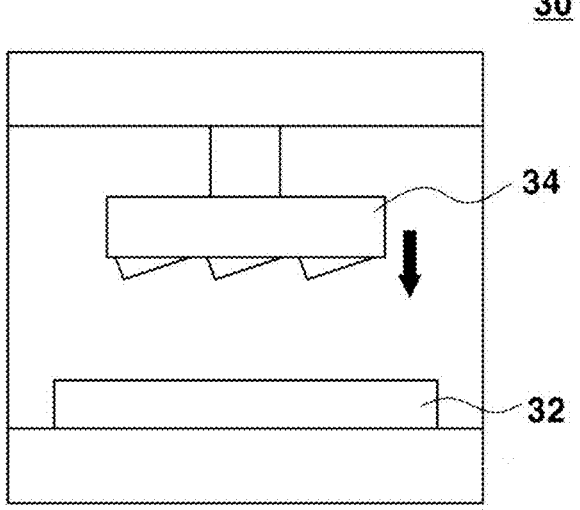
FIG. 1 is a block diagram of a system for diagnosing a dry electrode mixture according to some embodiments of the present disclosure.
FIG. 2A shows an example of a flow property measurement apparatus.

It should be understood that the appended drawings are not necessarily to scale, presenting a somewhat simplified representation of various preferred features illustrative of the basic principles of the disclosure. The specific design features of the present disclosure as disclosed herein, including, for example, specific dimensions, orientations, locations, and shapes, will be determined in part by the particular intended application and use environment.

In the figures, reference numbers refer to the same or equivalent parts of the present disclosure throughout the several figures of the drawing.

DETAILED DESCRIPTION

Specific structural or functional descriptions in embodiments of the present disclosure set forth in the description which follows will be exemplarily given to describe the embodiments of the present disclosure, and the present disclosure may be embodied in many alternative forms. Further, it will be understood that the present disclosure should not be construed as being limited to the embodiments set forth herein, and the embodiments of the present disclosure are provided only to completely disclose the disclosure and cover modifications, equivalents or alternatives which come within the scope and technical range of the disclosure.

In the following description of the embodiments, terms, such as "first" and "second", are used only to describe various elements, and these elements should not be construed as being limited by these terms. These terms are used only to distinguish one element from other elements. For example, a first element described hereinafter may be termed a second element, and similarly, a second element described hereinafter may be termed a first element, without departing from the scope of the disclosure.

When an element or layer is referred to as being "connected to" or "coupled to" another element or layer, it may be directly connected or coupled to the other element or layer, or intervening elements or layers may be present. In contrast, when an element or layer is referred to as being "directly connected to" or "directly coupled to" another element or layer, there may be no intervening elements or layers present. Other words used to describe relationships between elements should be interpreted in a like fashion, e.g., "between" versus "directly between," "adjacent" versus "directly adjacent," etc.

Wherever possible, the same reference numbers will be used throughout the drawings to refer to the same or like parts. The terminology used herein is for the purpose of describing particular embodiments only and is not intended to be limiting. As used herein, singular forms may be intended to include plural forms as well, unless the context clearly indicates otherwise. The terms "comprises," "comprising," "including," and "having" are inclusive and therefore specify the presence of stated features, integers, steps, operations, elements, components, and/or combinations thereof, but do not preclude the presence or addition of one or more other features, integers, steps, operations, elements, components, and/or combinations thereof.

Hereinafter, the present disclosure will be described in detail with reference to the accompanying drawings.

As described above, there is no established method of evaluating a dry electrode mixture for dry electrodes at present. Therefore, the dry electrode mixture should pass through a subsequent process to detect information on or determine the quality of the dry electrode mixture.

In order to acquire the information on the dry electrode mixture, various analytical instruments are being used. However, the instruments which are being used now may not provide immediate feedback during a process. Further, in terms of the dry electrode mixture which is compounded into a specific form depending on the purpose of film-forming, it is difficult to apply most particle analysis evaluation methods, in which measurement is performed in the state in which particles are dispersed in a solvent, to the dry electrode mixture.

Therefore, the present disclosure provides a system for diagnosing a dry electrode mixture, which may acquire the information on the dry electrode mixture using feature values of the dry electrode mixture as indicators through deep learning.

As shown in FIG. 1, a system 1 for diagnosing a dry electrode mixture may acquire the information on the dry electrode mixture. Concretely, the system 1 may provide the information on the dry electrode mixture using deep learning.

A deep learning model 10 of the system 1 may learn the information on dry electrode mixtures and may output a desired result value based on learning. In some examples of implementation, the deep learning model 10 of the system 1 according to the present disclosure may be trained through supervised learning in which inputs and outputs are provided together. In some examples of implementation, the deep learning model 10 of the system 1 may be based on an artificial neural network. The artificial neural network means a type of machine learning models which includes three or more layers and is based on the structure of a network in which neurons are connected by synapses. The artificial neural network includes a plurality of hidden layers disposed between an input layer and an output layer.

The deep learning model 10 is configured to learn the information on dry electrode mixtures. The information on the dry electrode mixtures includes feature values and manufacturing conditions of the dry electrode mixtures. In one example of implementation, the feature values of the dry electrode mixtures may include at least one of flowabilities or electrical conductivities of the dry electrode mixtures. Further, the manufacturing conditions of the dry electrode mixtures include the ratios of materials in the dry electrode mixtures, and the dispersion speeds and dispersion times of the dry electrode mixtures. The information on the dry electrode mixtures learned by the deep learning model 10 may be acquired from a plurality of dry electrode mixtures manufactured by a manufacturing apparatus 20. According to the present disclosure, the area under the ROC curve (AUC) of the deep learning model 10 is equal to or greater than 0.85.

Here, the dry electrode mixture includes an electrode active material, a conductive material, and a binder. A dry electrode may be manufactured from the dry electrode mixture and a current collector. According to the present disclosure, the system 1 may be applied not only to a lithium ion battery including a solid electrolyte but also to a lithium metal battery and an all-solid-state battery. According to one example of implementation, in case of a lithium ion battery, the dry electrode mixture may include 90 to 99 wt % of the electrode active material, 0.01 to 5 wt % of the conductive material, and 0.01 to 5 wt % of the binder. According to another example of implementation, in case of an all-solid-state battery, the dry electrode mixture may include 70 to 99 wt % of the electrode active material, 0.01 to 30 wt % of a solid electrolyte, 0.01 to 5 wt % of the conductive material, and 0.01 to 5 wt % of the binder. According to the present disclosure, the dry electrode may be a cathode or an anode.

In some examples of implementation, when a cathode is manufactured, the electrode active material includes a cathode-deactive material. As a non-limiting example, the cathode active material may be lithium nickel manganese cobalt oxide (NMC), lithium ferro-phosphate (LFP), lithium cobalt oxide (LCO), or sulfur. In some examples of implementation, when an anode is manufactured, the electrode active material includes an anode active material. As a non-limiting example, the anode active material may include graphite or silicon.

The conductive material may include carbon. Further, when a dry electrode mixture for all-solid-state batteries is manufactured, the dry electrode mixture may further include a polyethylene oxide (PEO)-based polymer electrolyte, an oxide-based solid electrolyte and/or a sulfide-based solid electrolyte.

The dry electrode mixture is manufactured by mixing the electrode active material, the conductive material and the binder by the manufacturing apparatus 20. The dry electrode mixture may pass through various mixing processes depending on the dispersion purpose thereof. For example, high shear mixing equipment using rotation or fluid mixing equipment using air may be used as the manufacturing apparatus 20. In some examples of implementation, the manufacturing apparatus 20 may include a chiller configured to control heat generated during mixing. The chiller may be operated within a temperature range of −20° C. to 20° C. Through the mixing process, manufacture of a half-finished product, which may be manufactured into a dry electrode, or the dry electrode mixture is completed.

In one example of implementation of the present disclosure, training data for the deep learning model 10 may be acquired by a flow property measurement apparatus 30. The flow property measurement apparatus 30 is configured to measure the flow property of the dry electrode mixture manufactured in the above-described manner. A flow property evaluation method, which is employed, may be executed based on American Society for Testing and Materials (ASTM) standard D6128.

FIG. 2A depicts an example flow property measurement apparatus 30. The mixture in a powder form is put in a tray 32 of the flow property measurement apparatus 30. The powder mixture is uniformly spread out.

The flow property measurement apparatus 30 includes a blade 34. When the flow property measurement apparatus 30 starts, the blade 34 located above the tray 32 operates. The blade 34 descends toward the tray 32 and contacts with the powder in the tray 32. The blade 34 applies minute shear stress to the powder by applying minute pressure to the powder mixture from the moment that the blade 34 contacts with the powder. A collapse may occur in the powder mixture at a certain point in time depending on the characteristics of the powder mixture, and a stress at this point in time may be measured as internal force data. When the collapse occurs, a shear stress is applied to the powder mixture by applying a slightly higher pressure to the powder mixture, and internal force data is measured again.

Under this evaluation method, shear stress is applied to a designated amount of the dry electrode mixture, and internal force of the dry electrode mixture in an equilibrium state or in a steady state flow is measured. The internal force of the mixture in the equilibrium state may indicate distribution of force varied depending on friction and cohesion between particles in the mixture. The flow index of the mixture may be quantified based on such measurement. For example, the flow index of the mixture may be acquired by differentiating the measured internal force with respect to the shear stress. The friction and cohesion between the particles may be varied depending on the degree of dispersion of the dry electrode mixture or the degree of fibrillization of the binder, and these characteristics may be confirmed through the flow property evaluation method.

Hereinafter, flow property evaluation will be executed based on ASTM standard D6128. For example, a mixture for positive electrodes will be described. The mixture is acquired by putting a positive electrode active material, such as NMC811 or NMC622, graphite, a binder, etc., into the mixing apparatus 20, and setting mixing conditions, such as a mixing time (h), a mixing temperature (° C.), a mixing speed (m/s), and a gap (mm) between a mixing chamber and blades. Here, the dry electrode mixture may be acquired under a single mixing condition or a plurality of mixing conditions, as described above. Thereafter, flow property analysis of the dry electrode mixture is performed.

Figure 3:
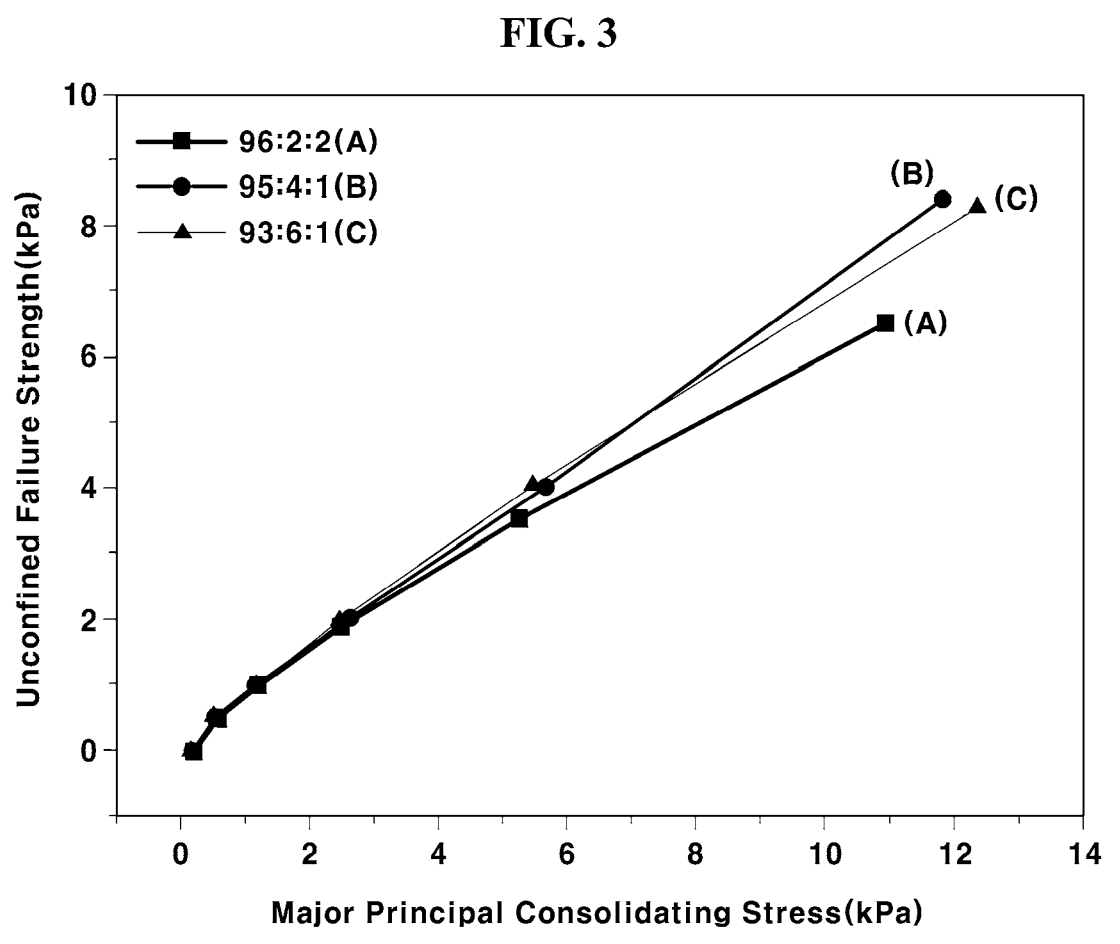

FIG. 3 is a graph representing results of flow property evaluation of arbitrary dry electrode mixtures depending on ratios among respective materials in the dry electrode mixtures. Dry electrode mixtures A, B and C are manufactured using lithium nickel manganese cobalt oxide as an electrode active material, polytetrafluoroethylene (PTFE) as a binder, and carbon black as a conductive material. The ratio of the electrode active material to the binder to the conductive material is 96:2:2 in dry electrode mixture A, is 95:4:1 in dry electrode mixture B, and is 93:6:1 in dry electrode mixture C. The degree of fibrillization of the binder is set to the same value. In this case, it may be confirmed that the ratio among the respective materials in the dry electrode material affects the flow property of the dry electrode material.

In flow property evaluation, shear stress is applied to the respective dry electrode mixtures, and the internal forces of the dry electrode mixtures in the equilibrium state are measured. When a collapse occurs in agglomerated powder at the applied shear stress, the result at this point is recorded. Such a process at a higher shear stress is repeated. Through measurement in this way, the applied shear stress is represented as Major Principal Consolidating Stress on the X-axis, and the point at which the collapse occurs in the equilibrium state is represented as Unconfined Failure Strength on the Y-axis. The data of X-axis values and Y-axis values may be acquired as a 2×N matrix (N being a natural number of 3 or more). The measured 2×N matrix is used as input variables (or feature values) of the deep learning model 10.

Figure 4A:
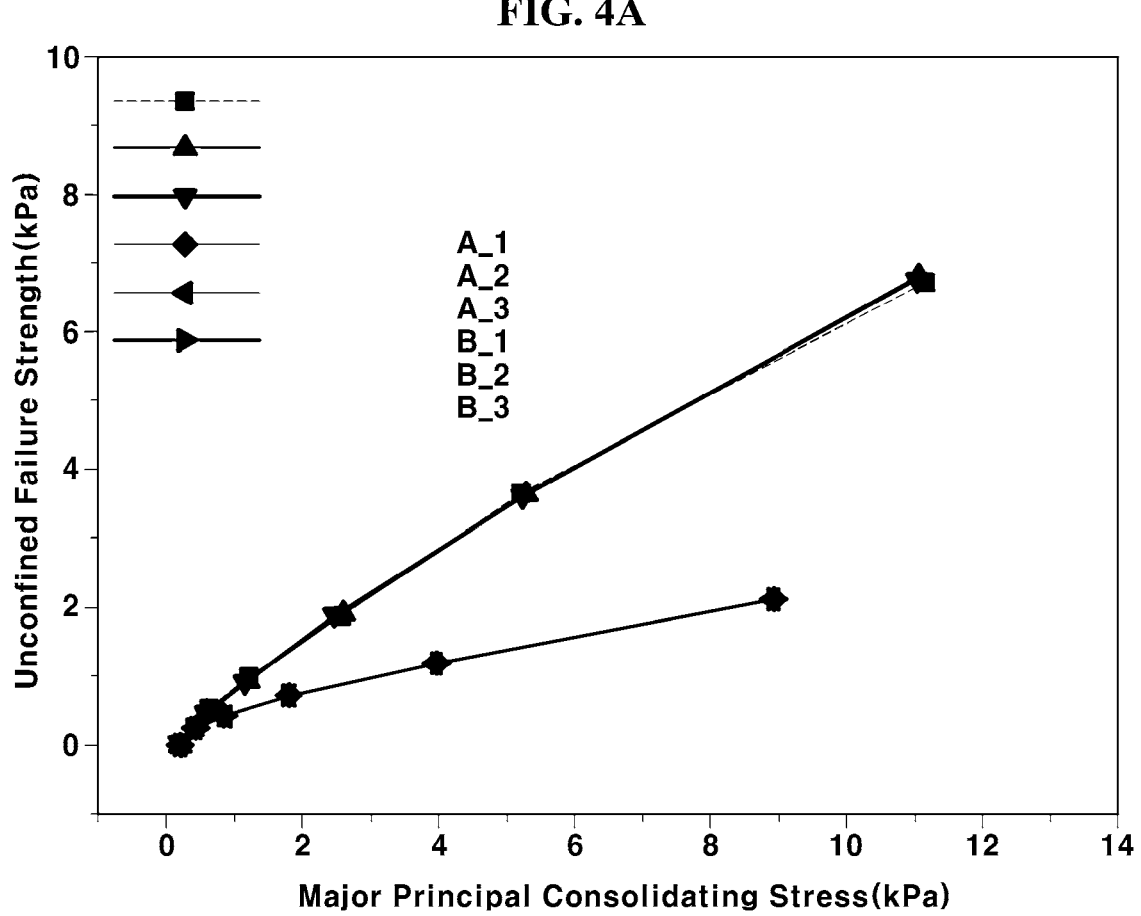
Figure 4B:
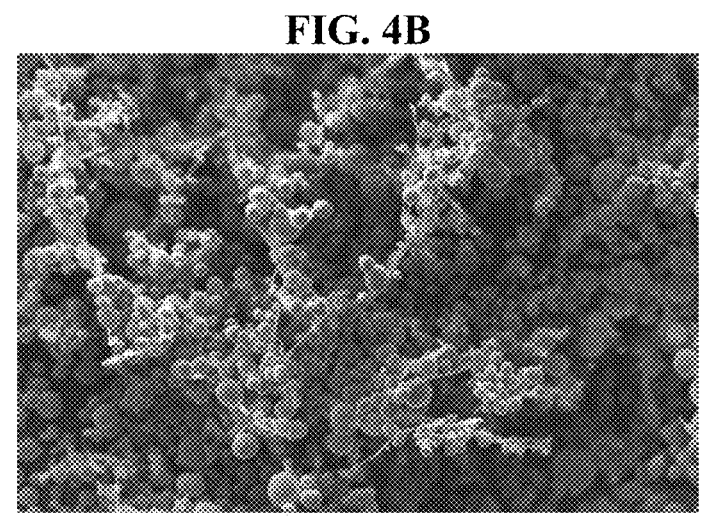
Figure 4C:
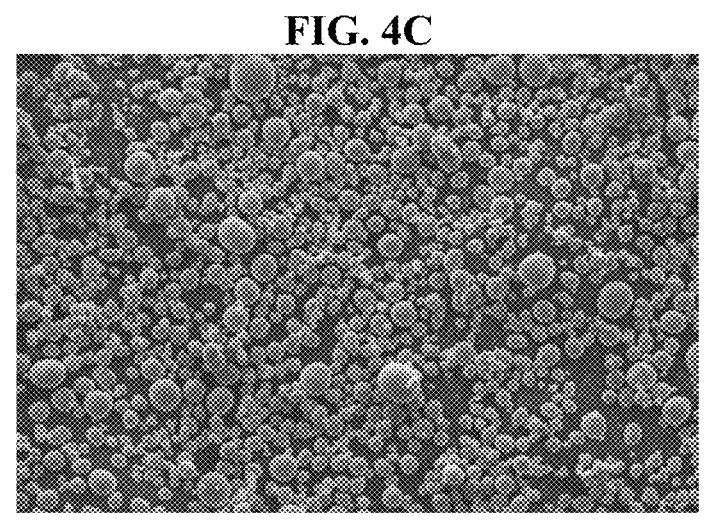

FIGS. 4A, 4B and 4C show results of flow property evaluation of certain dry electrode mixtures depending the degree of fibrillization of a binder based on the dispersion speed and the dispersion time. The ratio among materials in the dry electrode mixtures is fixed, and the degree of the fibrillization of the binder in the dry electrode mixtures is varied. In the dry electrode mixtures, the ratio of an electrode active material to the binder to a conductive material is set to 96:2:2. FIG. 4B depicts the scanning electron microscopy (SEM) image of samples A1, A2 and A3, and FIG. 4C depicts the scanning electron microscopy (SEM) image of samples B1, B2, and B3.

Samples A1, A2 and A3, in which the binder is well fibrillized due to sufficient dispersion speed and time, is capable of being formed as a film, while samples B1, B2, and B3, in which the binder is scarcely fibrillized, is not capable of being formed as a film. A distinction between two groups of samples due to fibrillization of the binder may be clearly made through flow property evaluation. In FIG. 4A, samples A1, A2 and A3 indicate samples A which are manufactured three times under the same conditions, and it may be confirmed that samples A1, A2 and A3 have excellent reproducibility. Further, samples B1, B2, and B3 indicate samples B which are manufactured three times under the same conditions, and it may be confirmed that samples B1, B2, and B3 also have excellent reproducibility.

According to one example of implementation of the present disclosure, training data for the deep learning model 10 may be provided by an electrical conductivity measurement apparatus 40. The electrical conductivity of the dry electrode mixture may be acquired by measuring the resistance of the dry electrode mixture while changing a pressure applied to the dry electrode mixture. Concretely, measurement of the electrical conductivity of the dry electrode mixture is performed through a method in which a pressure is applied to a designated amount (mass) or a designated form (volume) of the dry electrode mixture. As a non-limiting example, the resistance of the dry electrode mixture at each pressure may be measured while applying a pressure from 1 to 100 kilonewtons to the dry electrode mixture. The binder in the dry electrode mixture is a resistance element, and the electrical conductivity characteristics of the dry electrode mixture are varied depending on the materials in the dry electrode mixture. Therefore, a minute difference varied depending on the degree of dispersion of the dry electrode mixture and the degree of fibrillization and distribution of the binder may be evaluated through the electrical conductivity of the dry electrode mixture.

Figure 2B:
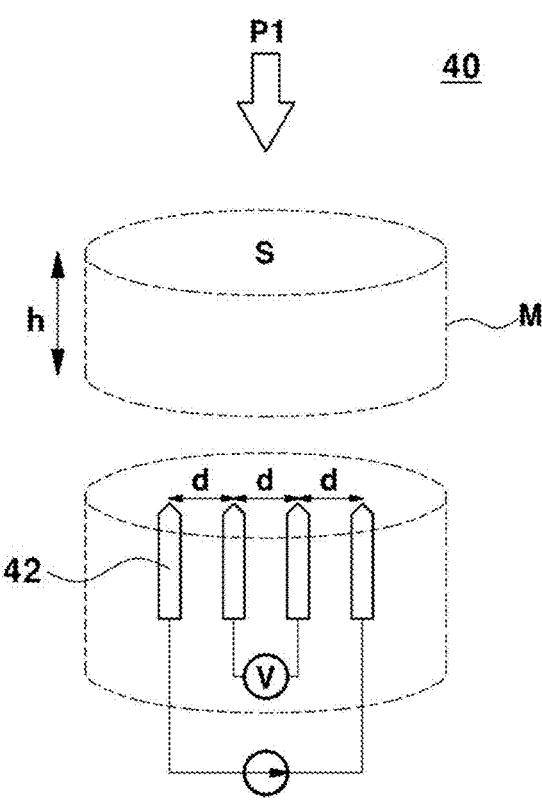
FIG. 2B shows an example of an electrical conductivity measurement apparatus.

FIG. 2B shows an example of an electrical conductivity measurement apparatus 40. The electrical conductivity measurement apparatus 40 may measure an electrical conductivity of a dry electrode mixture M while applying a predetermined or varying pressure. The dry electrode mixture is prepared with a fixed volume with an area S and a height h or with a fixed mass. A certain pressure P1 is applied from the top of the dry electrode mixture M with the specified amount, and the electrical conductivity is measured from below by a probe 42. The electrical conductivity, e.g., siemens per centimeter, with respect to pressure, e.g., in kilonewton, are measured. The measured data may be used in evaluating the dry electrode mixture M.

As described above, flow property is very effective in evaluation of the half-finished product of the dry electrode mixture, but it may be difficult to evaluate samples manufactured under some conditions through flow property. The inventor(s) of the present disclosure has found that measurement of electrical conductivity may improve accuracy of evaluation.

Figure 5:
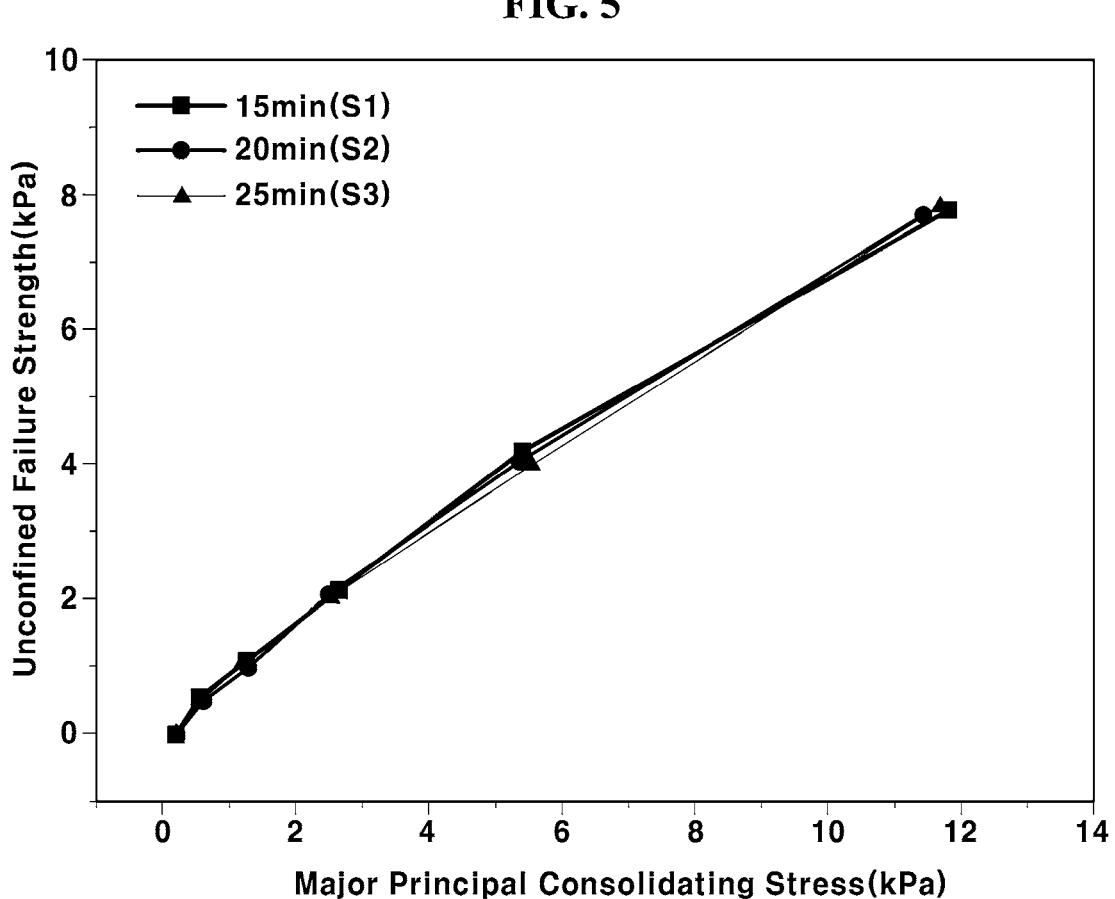
FIG. 5 is a graph representing results of flow property evaluation of certain dry electrode mixtures.

Concretely, FIG. 5 represents results of flow property evaluation of samples S1, S2, and S3, acquired by dispersing an electrode active material and a conductive material for 15 minutes (S1), 20 minutes (S2), and 25 minutes (S3), respectively, and then adding a binder thereto so as to be dispersed therein. In this case, it may be confirmed that it is difficult to distinguish dry electrode mixtures from one another through flow property evaluation, and it is also difficult to distinguish the dry electrode mixtures from one another through scanning electron microscopy (SEM).

Figures 6, 7:
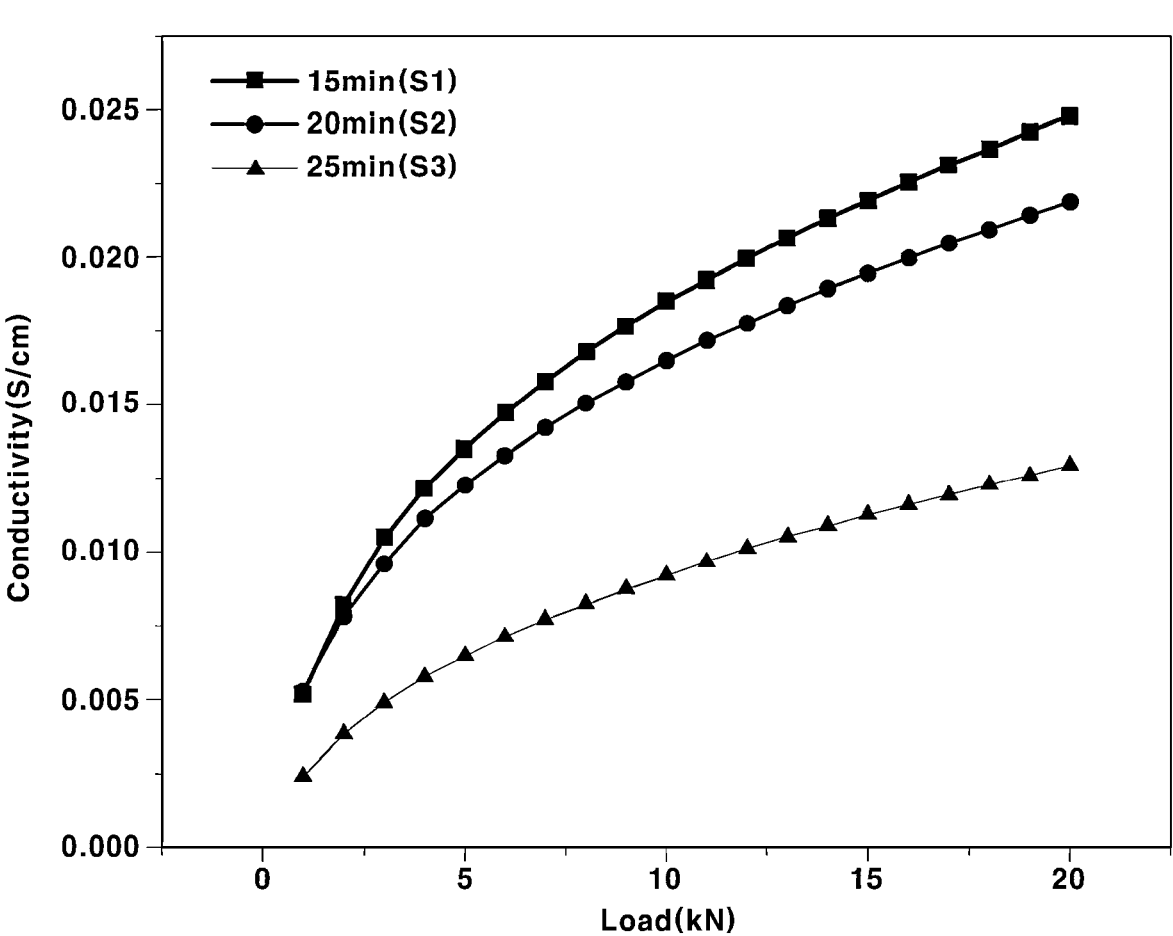
FIG. 6 is a graph representing results of electrical conductivity measurement of the certain dry electrode mixtures.
FIG. 7 is a flowchart representing generation of a deep learning model of the system according to some embodiments of the present disclosure.

On the other hand, as shown in FIG. 6, it may be confirmed that the three samples S1, S2 and S3 may be distinguished from one another through electrical conductivity even if a difference of the binder content is only 0.01%. Therefore, according to some examples of implementation of the present disclosure, the manufacturing conditions of the dry electrode mixture may be predicted based on both results of flow property evaluation and electrical conductivity.

The system 1 may include a controller 50. The controller 50 may include a processor 70 and a memory 60. Operation of the system 1 may be executed by the controller 50 including the processor 70 and the memory 60.

Commands, which may be executed by the processor 70, are stored in the memory 60. The commands may include commands configured to execute operation of the processor 70 and/or operation of respective elements of the processor 70.

The memory 60 may be a volatile or non-volatile memory. As a non-limiting example, the volatile memory may be a dynamic random access memory (DRAM), a static random access memory (SRAM), or the like. As another non-limiting example, the non-volatile memory may be an electrically erasable programmable read-only memory (EE-PROM), a flash memory, a magnetic RAM, a CD-ROM, a DVD-ROM, or the like.

Further, the memory 60 may store a matrix in which operations included in the neural network will be executed. The memory 60 may store results of the operations, executed by the processor 70.

The processor 70 may execute the commands stored in the memory 60. The processor 70 may execute computer readable code and the commands stored in the memory 60. As a non-limiting example, the processor 70 may be a central processing unit, a graphics processing unit, a neural processing unit, a multi-core processor, a multi-processor, an application-specific integrated circuit (ASIC), or a field programmable gate array (FPGA).

According to some embodiments of the present disclosure, the system 1 may be implemented in the form of a recording medium including commands executable by computers, such as a program module executed by computers. Computer readable media may be arbitrary available media accessible by computers, and may include volatile and non-volatile media and removable and non-removable media. Further, the computer readable media may include all computer storage media. The computer storage media may include volatile and non-volatile media and removable and non-removable media implemented by arbitrary methods or techniques to store information, such as computer readable commands, data structures, program modules or other data.

Hereinafter, establishment of the system 1 and a process of operating the system 1 will be described.

As shown in FIG. 7, data on dry electrode mixtures is collected at S60. Manufacturing conditions C2 including ratios of materials in the respective dry electrode mixtures and the dispersion speeds and dispersion times of the respective dry electrode mixtures are collected. Further, feature values C1 of flowabilities and/or electrical conductivities of the respective dry electrode mixture are measured, and the measured information is collected.

The deep learning model 10 of the system 1 is trained using the collected data at S62. As shown in FIG. 8, the input variable of the deep learning model 10 is set to the feature value C1, and the output variable of the deep learning model 10 is set to the manufacturing conditions C2. That is, the deep learning model 10 is trained using the feature values C1 as the input variables and the manufacturing conditions C2 as the output variables through deep learning using a neural network model. Thereby, the deep learning model 10 of the system 1 is generated in S64.

As shown in FIG. 9, the system 1 receives a feature value C1 at S80. The deep learning model 10 of the system 1 is configured to predict the manufacturing conditions C2 of a dry electrode mixture having the input feature value C1 at S82. The predicted manufacturing conditions C2 are fed back to the manufacturing apparatus 20 to be reflected in manufacture of the dry electrode mixture at S84.

According to the present disclosure, when flow property and electrical conductivity of a certain dry electrode mixture are given in the state in which the dispersion time and dispersion speed of the dry electrode mixture and the ratio of materials included in the dry electrode mixture are not known, the system 1 may provide corresponding manufacturing conditions, and the manufacturing conditions may be fed back to the manufacturing apparatus 20.

Since a dry electrode manufactured by the dry process has very strict dispersion conditions, as compared to a wet electrode manufactured by the wet process using a solvent, in order to control quality of the dry electrode at the time of mass production, information on a dry electrode mixture should be easily processed. The present disclosure may provide a system which diagnoses a dry electrode mixture manufactured by acquiring data through flow property and electrical conductivity measurement and performing training through deep learning using a neural network model. Accuracy in quality evaluation increases as more and more data is accumulated in the above-suggested way, and thereby, the system according to the present disclosure may be of great help to construction of a fully automated production method in which conditions in a previous stage are easily controlled through automatic algorithms without human judgement in the process of mass production.

As is apparent from the above description, the present disclosure provides a system for diagnosing a dry electrode mixture, which may evaluate inherent conditions of the dry electrode mixture only using physical feature values through machine learning.

The disclosure has been described in detail with reference to preferred embodiments thereof. However, it will be appreciated by those skilled in the art that changes may be made in these embodiments without departing from the principles and spirit of the disclosure, the scope of which is defined in the appended claims and their equivalents.

The invention claimed is:

1. A method of manufacturing a dry electrode mixture, comprising:

determining a feature value of a first dry electrode mixture;

providing the feature value of the first dry electrode mixture to a deep learning model, wherein the deep learning model is configured to determine a manufacturing condition of the first dry electrode; and manufacturing a second dry electrode mixture based on the manufacturing condition, wherein the first and second dry electrode mixtures are formed by mixing an electrode active material, a conductive material and a binder without a solvent.

2. The method of claim 1, wherein the feature value comprises one or more of a flow index indicating flow property of the first dry electrode mixture and electrical conductivity of the first dry electrode mixture.

3. The method of claim 1, wherein the manufacturing condition comprises one or more of a dispersion speed of the first dry electrode mixture, a dispersion time of the first dry electrode mixture, or a ratio of materials in the first dry electrode mixture.

4. The method of claim 1, wherein the deep learning model is constructed by training using data on a plurality of dry electrode mixtures.

5. The method of claim 4, wherein the data comprise measured feature values and used manufacturing conditions of the plurality of dry electrode mixtures; and wherein the measured feature values are set to input variables, and the used manufacturing conditions are set to output variables.

6. The method of claim 1, wherein a weight ratio of the electrode active material to the conductive material to the binder is 90 to 99:0.01 to 5:0.01 to 5.

7. A system for manufacturing a dry electrode mixture, the system comprising:

a mixer;

a memory comprising commands; and a processor configured to communicate with the mixer and execute the commands, wherein the processor executes the commands to:

receive a feature value of a first dry electrode mixture;

input the feature value to a deep learning model;

receive a manufacturing condition of the first dry electrode mixture from the deep learning model; and operate the mixer based on the manufacturing condition to manufacture a second dry electrode mixture, wherein the first and second dry electrode mixtures are formed by mixing an electrode active material, a conductive material and a binder without a solvent.

8. The system of claim 7, wherein the feature value comprises one or more of a flow index indicating flow property of the first dry electrode mixture and electrical conductivity of the first dry electrode mixture.

9. The system of claim 8, wherein the flow index is determined based on internal force of the first dry electrode mixture, measured depending on shear stress applied to the first dry electrode mixture.

10. The system of claim 8, wherein the electrical conductivity is determined based on resistance of the first dry electrode mixture, measured while applying a pressure to the first dry electrode mixture.

11. The system of claim 7, wherein the manufacturing condition comprises one or more of a dispersion speed of the first dry electrode mixture, a dispersion time of the first dry electrode mixture, and a ratio of materials in the first dry electrode mixture.

12. A system for manufacturing a dry electrode mixture, the system comprising:

a mixer;

a flow property measurement apparatus configured to evaluate flow property of a first dry electrode mixture;

an electrical conductivity measurement apparatus configured to measure electrical conductivity of the first dry electrode mixture; and a controller configured to receive one or more of the flow property and the electrical conductivity of the first dry electrode mixture and to output a manufacturing condition of the first dry electrode mixture based on a deep learning model, wherein the controller is configured to operate the mixer based on the manufacturing condition to manufacture a second dry electrode mixture, wherein the first and second dry electrode mixtures are formed by mixing an electrode active material, a conductive material and a binder without a solvent.

13. The system of claim 12, wherein the flow property measurement apparatus is configured to apply shear stress to the first dry electrode mixture and to evaluate the flow property of the first dry electrode mixture based on internal force of the first dry electrode mixture, measured depending on the applied shear stress.

14. The system of claim 12, wherein the electrical conductivity measurement apparatus measures the electrical conductivity of the first dry electrode mixture based on resistance of the first dry electrode mixture, measured while changing a pressure applied to the first dry electrode mixture.

15. The system of claim 12, wherein the deep learning model is generated by training using feature values and manufacturing conditions of a plurality of dry electrode mixtures and is configured such that the feature values are set to input variables and the manufacturing conditions are set to output variables.

16. The system of claim 12, wherein the first dry electrode mixture or the second dry electrode mixture is applied to lithium ion battery, a lithium metal battery, or an all-solid-state battery.

\* \* \* \* \*